United States Patent

Woods et al.

[11] 3,947,478
[45] Mar. 30, 1976

[54] ALKYLATED 3,20-DIKETO-Δ⁴-STEROIDS OF THE PREGNANE SERIES

[75] Inventors: Gilbert Frederick Woods, Glasgow; James Cairns, Cumbernauld; George McGarry, Airdrie, all of Scotland

[73] Assignee: Akzona Incorporated, Asheville, N.C.

[22] Filed: Nov. 22, 1974

[21] Appl. No.: 526,204

Related U.S. Application Data

[63] Continuation-in-part of Ser. No. 320,777, Jan. 3, 1973, Pat. No. 3,862,194.

[30] Foreign Application Priority Data

Jan. 12, 1972 United Kingdom............. 1534/72

[52] U.S. Cl. ..... 260/397.3; 260/397.4; 260/397.45; 424/243; 260/239.55 R
[51] Int. Cl.² ......................................... C07J 1/00
[58] Field of Search.................. 260/397.3, 397.45

[56] References Cited
UNITED STATES PATENTS 3,862,194    1/1975    Woods et al................. 260/397.45

Primary Examiner—Elbert L. Roberts
Attorney, Agent, or Firm—Francis W. Young; Philip M. Pippenger; Hugo E. Weisberger

[57] ABSTRACT

The invention relates to novel alkylated steroids of the pregnane series having the formula:

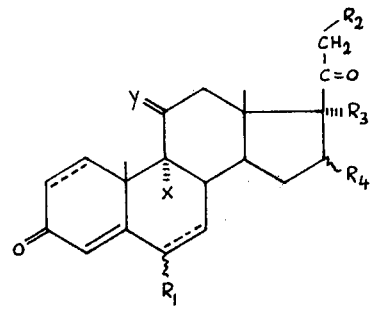

wherein
X = a member of the group consisting of H and halogen;
Y = a member of the group consisting of $H_2$, H(OH), H(OAcyl) and O;
$R_1$ = a member of the group consisting of H, $CH_3$ and halogen;
$R_2$ = alkyl having 1–4 carbon atoms;
$R_3$ = a member of the group consisting of H (except when Y = $H_2$), OAcyl, Oalkyl, and $CH_3$;
$R_4$ = a member of the group consisting of H and alkyl having 1–4 carbon atoms and in which at least one of the substituents $R_3$ and $R_4$ is alkyl; and
$C_1$–$C_2$ and $C_6$–$C_7$ are selected from a saturated and an unsaturated bond.

The novel compounds possess strong anti-inflammatory properties and are useful in the treatment of inflammatory conditions especially those associated with the skin and allergic reactions.

11 Claims, No Drawings

ALKYLATED 3,20-DIKETO-Δ⁴-STEROIDS

CROSS-REFERENCE TO RELATED APPLICATION

This application is a continuation-in-part of application Ser. No. 320,777, filed Jan. 3, 1973, now U.S. Pat. No. 3,862,194 issued Jan. 21, 1975.

The present invention relates to novel alkylated steroids of the pregnane series.

More particularly, the invention relates to novel alkylated steroids of the formula:

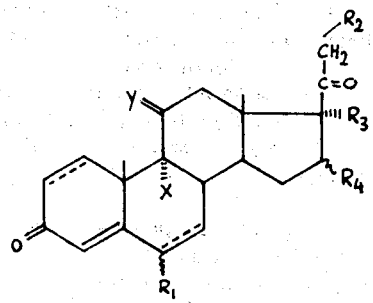

, wherein
X = a member of the group consisting of H and halogen;
Y = a member of the group consisting of $H_2$, H(OH), H(OAcyl) and O;
$R_1$ = a member of the group consisting of H, $CH_3$ and halogen;
$R_2$ = alkyl having 1–4 carbon atoms, preferably $CH_3$ or $C_2H_5$;
$R_3$ = a member of the group consisting of H (except when Y = $H_2$), OAcyl, OAlkyl and $CH_3$, preferably OAcyl or $CH_3$;
$R_4$ = a member of the group consisting of H and alkyl having 1–4 carbon atoms, preferably $CH_3$, and in which at least one of the substituents $R_3$ and $R_4$ is alkyl; and $C_1$–$C_2$ and $C_6$–$C_7$ are selected from a saturated and an unsaturated bond.

The novel compounds of the invention possess strong anti-inflammatory properties when applied locally and cause little or no systemic, thymolytic, adrenolytic and salt-retaining effects. Consequently, they are very useful in the treatment of inflammatory conditions especially those associated with the skin and allergic reactions. These compounds can be administered topically in the form of ointments, creams, lotions or sprays and suppositories or by injection for instance intraarticularly for the local treatment of inflammation, possibly in combination with other active ingredients.

The compounds according to the invention may be prepared by 21-alkylation of 20-keto compounds of the pregnane series having the partial formula:

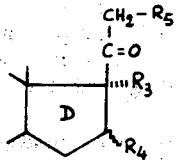

, wherein
$R_3$ = H, OH, OAlkyl, OAcyl or $CH_3$,
$R_4$ = H or an alkyl group having 1–4 carbon atoms, and at least one of the substituents $R_3$ and $R_4$ is an alkyl group, and $R_5$ = H, except where the enolate ion is generated with Grignard reagent in which case it may be H or halogen.

Other substituents indicated in the formula of the end-products may be introduced subsequently by methods known per se.

21-Alkylation of a 20-keto pregnane has been carried out via the Mannich reaction by treating a 20-keto-pregnane with the salt of an amine, preferably a low alkyl amine, in the presence of formaldehyde, and converting the thus formed 21-aminomethyl compound into a quaternary ammonium derivative which is converted into a 21-methylene compound by treatment with base, and the 21-methylene derivative is either reduced catalytically to the desired 21-methyl compound or converted by 1,4-ignardation to a 21-alkyl derivative. The drawback of this procedure is that yields are low.

We have found that known procedures for alkylating simple ketones for example forming the enolate salt with trityl lithium or with lithium dialkylamide, such as lithium diethylamide and preferably lithium di-isopropylamide, followed by treatment with an alkyl halide, may also be applied to 20-keto-pregnanes to furnish the 21-alkyl derivatives in high yield.

An alternative method of 21-alkylation is to treat a 20-keto pregnane as defined above with a Grignard reagent in which case instead of the anticipated normal Grignard reaction at the 20-keto group the $\Delta^{20}$-enolate salt of the Grignard complex is formed and this may be alkylated at C-21 by treatment with an alkyl halide, preferably an alkyl iodide. In this method, when $R_3$ = H, $R_5$ is preferably halogen.

It is also possible to form the 21-alkyl derivatives from 20-keto pregnanes as defined above by reacting them with an alkali metal such as sodium or an alkali metal amide such as sodamide in a suitable solvent such as liquid ammonia followed by reaction with an alkyl halide, preferably an alkyl iodide. This method is, however, more suited to the preparation of 21,21-dialkyl derivatives in which case an excess of reagents may be used. When approximately one equivalent of alkali metal or alkali metal amide is used the product is a mixture from which the 21-mono-alkyl derivative can be separated as the main product.

In these alkylating procedures, if the starting material as defined above, contains a free hydroxyl group at C-17, this may become alkylated during the reaction sequence. However, a final product containing a free 17-hydroxyl group may be obtained by carrying out the 21-alkylation procedure on a 17-acyloxy derivative and hydrolysing the ester group under carefully controlled basic conditions after completion of the 21-alkylation.

Starting materials for the preparation of the compounds according to the invention are for example 20-keto pregnanes of the formula:

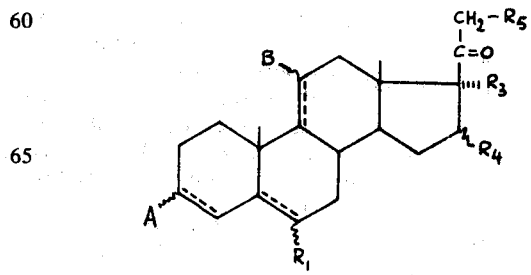

, wherein $R_1$, $R_3$, $R_4$ and $R_5$ have the meanings defined above,

A = a protected hydroxyl or keto group,
B = hydrogen or a protected α- or β-hydroxyl group, and $C_3$–$C_4$, $C_5$–$C_6$ and $C_9$–$C_{11}$ may be saturated or unsaturated.

During the alkylation procedure, it is preferable to protect an oxygen function at C-3 if one is present by reversible ether formation such as the tetrahydropyranyl ether in the case of a 3-hydroxyl group or a $\Delta^{3,5}$-enol ether in the case of a $\Delta^4$-3-keto grouping, or by ketal formation such as the dimethyl ketal in the case of a 3-keto group to prevent unwanted alkylation reactions such as O-alkylation which would take place at the same time as 21-alkylation if the starting material contained a free 3-hydroxyl group or a 3-acyloxy group or to prevent unwanted C-alkylation reactions from taking place in the α-position to a free 3-keto group if such were present. It has been found that the 3-O-alkylation products which are formed if a free 3-hydroxyl group or its acyl derivative is present during the alkylation reaction are very difficult to hydrolyse back to the desired 3-hydroxyl group which is a necessary precursor for converting to the 3-keto group in the final products according to the invention.

Similarly it is necessary to protect an 11-hydroxyl substituent if one is present in the starting material before carrying out the alkylation procedure to prevent the simultaneous formation of an 11-O-alkylated derivative which cannot be readily converted back to the free hydroxyl group. When an 11α-hydroxyl group is present, it is preferable to protect it by reversible ether formation such as the tetrahydropyranyl ether but when an 11β-hydroxyl substituent is present, because of its very sterically hindered position in the steroid molecule it is sufficient to protect it as an ester such as the acetate in which case the acyl group may itself undergo alkylation.

After introduction of the 21-alkyl substituent by the methods already described, other groups already present in the starting materials may be modified and new groups or functions may be introduced by methods known per se to furnish the desired end-products according to the invention.

A 3-hydroxyl group may be oxidized after hydrolysis of the protecting ether group, for example, by Oppenauer oxidation in the case of a $\Delta^5$-steroid to furnish a $\Delta^4$-3-keto steroid, or with chromic acid in the case of either a 5α- or 5β-3-hydroxy derivative to give the corresponding saturated 3-ketone.

Where a 3-keto group in the starting material is protected as its ketal derivative, or in the case of a $\Delta^4$-3-ketone, as the enol-ether for the purposes of the alkylation reaction, it is only necessary to hydrolyse it to regenerate the keto group.

In compounds containing a $\Delta^4$-3-keto grouping, additional double bonds may be introduced at positions $C_1$–$C_2$ and/or $C_6$–$C_7$ by known chemical means such as by reaction with suitable quinone derivatives or microbiologically with an appropriate micro-organism.

A 3-keto-5α-steroid may be converted to a $\Delta^{1,4}$-3-keto steroid by means of selenium dioxide or by reaction with a quinone such as dichlorodicyanobenzoquinone or by halogenation at positions 2 and 4 and subsequent dehydrohalogenation by methods known per se.

A 3-keto-5β-steroid may be converted into a $\Delta^4$-3-keto steroid by means of selenium dioxide or by monobromination at position 4 followed by dehydrobromination and the so formed $\Delta^4$-3-ketone may be transformed into the $\Delta^{1,4}$-3-ketone by further reaction with selenium dioxide or dichlorodicyanobenzoquinone. Alternatively, a 3-keto-5β-steroid may be converted directly into a $\Delta^{1,4}$-3-ketone by reaction with selenium dioxide or by reaction with a suitable quinone such as dichlorodicyanobenzoquinone, or by di-halogenation for example di-bromination at positions 2 and 4 subsequent dehydrohalogenation by methods known per se.

A $\Delta^4$-3-keto steroid may be converted into the corresponding $\Delta^6$-derivative by reaction with a suitable quinone such as chloranil and the thus formed $\Delta^{4,6}$-3-keto compound may then be converted to the corresponding $\Delta^{1,4,6}$-3-keto derivative by reaction with an appropriate quinone such as dichlorodicyanobenzoquinone.

The microbiological introduction of a double bond at position $C_1$–$C_2$ may be carried out by incubation with a 1,2-dehydrogenating micro-organism, for example coryn-bacterium Simplex, Bacillus sphaericus of Bacillus subtilis.

Introduction of a 6-substituent, if not already present may be effected if desired by converting a 3-hydroxy-$\Delta^5$-steroid into the 5α,6α-epoxide and treating the latter with methyl magnesium halide, a halogen acid, boron trifluoride or fluoroboric acid to give in each case the corresponding 5α-hydroxy-6β-substituted derivative which can then be converted into the corresponding $\Delta^4$-3-keto-6β-substituted compound by oxidising the 3-hydroxy-group with, for example, chromic acid and dehydrating the 5-hydroxy group appropriately under acid or basic conditions. Isomerisation of the 6β-substituent may be brought about my treatment with acid or base.

A $\Delta^{9(11)}$-double bond if present may be converted to the 9α-bromo-11β-hydroxy compound or an ester thereof by methods known per se and then transformed under basic conditions into a 9β,11β-epoxide which may be subsequently opened with a halogen acid to give the corresponding 9α-halo-11β-hydroxy derivative which can then be oxidised to the corresponding 9α-halo-11-ketone.

Introduction of an 11-hydroxyl group may be performed microbiologically, e.g. by incubation with an 11-hydroxylating micro-organism such as Curvularia or a Rhizopus after which the 11-hydroxyl group may be oxidised to an 11-keto group, acylated or dehydrated to form a $\Delta^{9(11)}$-double bond.

After elaboration of the $\Delta^{1,4}$-3-keto group an 11β-acyloxy group, if present, may be hydrolysed to the corresponding 11β-hydroxy derivative under relatively mild conditions with alcoholic alkali and the so formed 11β-hydroxy group may then be oxidised if desired to the corresponding 11-ketone.

A 17α-hydroxy group, if present, is acylated with an organic carboxylic acid with 1–18 C-atoms or a functional derivative thereof such as the anhydride or the halide.

As said before the compounds of the present invention possess strong anti-inflammatory properties. In the "Human Vasoconstriction Test" the compounds of the present invention have an ED-50 in alcohol in the range of 4 to 6.5, indicating a good to excellent potency. ED-50 = — log (concentration in g/ml in alcohol, at which concentration 50% of the counts is positive). In comparative tests ED-50 of dexamethasone was 4.4 and of betamethasone 17-valerate was 6.2.

In various tests for determining the anti-inflammatory activity the compounds of the present invention exhibit excellent local activity and low or no systemic, thymolytic or adrenolytic effects, as can be seen from the following data. Data of the well-known anti-inflammatory compound dexamethasone are also stated, for comparison.

Rat paw kaolin edema test (local application)

A = 11$\beta$-hydroxy-16$\alpha$,17$\alpha$,21-trimethyl-$\Delta^{1,4}$-pregnadiene-3,20-dione.

B = dexamethasone.

| Compound | Dose mg/paw | edema % after 4 hr | % after 24 hr | thymus % after 72 hrs | adrenals % after 72 hrs |
|---|---|---|---|---|---|
| A | 0.05 mg | −37 | −78 | +6 | −5 |
| B | 0.05 mg | −111 | −47 | −68 | −6 |
| A | 0.8 mg | −33 | −80 | −4 | +5 |
| B | 0.8 mg | −83 | −115 | −89 | −42 |

Granuloma test (local application) in rats

Left paw: cotton pellet impregnated with carragenin
Right paw: cotton pellet impregnated with carragenin + 0.1 mg A
Granuloma tissue % change: left paw + 1; right paw −82.

Modified carragenin pouch test (local application) in rats

| Compound | Dose mg/kg | exsudate % change | thymus % change | adrenals % change |
|---|---|---|---|---|
| A | 0.4 | −67 | +4 | +2 |
| B | 0.2 | −61 | −72 | −11 |

From the above data it is clear that the novel compound has excellent local anti-inflammatory activity and no or low systemic, thymolytic and adrenolytic effects.

Rat paw kaolin edema test (systemis vs local)

Compounds according to the invention:
a. 11$\beta$-acetoxy-16$\alpha$,17$\alpha$,21-trimethyl-$\Delta^{1,4}$-pregnadiene-3,20-dione
b. 11$\beta$-hydroxy-16$\alpha$,17$\alpha$,21-trimethyl-$\Delta^{4}$-pregnene-3,20-dione
c. 6$\alpha$,16$\alpha$,17$\alpha$,21-tetramethyl-11$\beta$-hydroxy-$\Delta^{1,4}$-pregnadiene-3,20-dione
d. 9$\alpha$-fluoro-11$\beta$-hydroxy-16$\alpha$,17$\alpha$,21-trimethyl-$\Delta^{4,6}$-pregnadiene-3,20-dione
e. 9$\alpha$-fluoro-11$\beta$-hydroxy-16$\alpha$,17$\alpha$,21-trimethyl-$\Delta^{1,4,6}$-pregnatriene-3,20-dione
f. 9$\alpha$-chloro-11$\beta$-hydroxy-16$\alpha$,17$\alpha$,21-trimethyl-$\Delta^{1,4}$-pregnadiene-3,20-dione
g. 9$\alpha$-fluoro-16$\alpha$,17$\alpha$,21-trimethyl-$\Delta^{1,4}$-pregnadiene-3,11,20-trione
h. 9$\alpha$-fluoro-11$\beta$-hydroxy-16$\alpha$,17$\alpha$-dimethyl-21-ethyl-$\Delta^{1,4}$-pregnadiene-3,20-dione
i. 9$\alpha$-fluoro-11$\beta$,17$\alpha$-dihydroxy-16$\alpha$,21-dimethyl-$\Delta^{1,4}$-pregnadiene -3,20-dione 17$\alpha$-propionate
j. 11$\beta$-hydroxy-16$\alpha$,17$\alpha$,21,21-tetramethyl-$\Delta^{1,4}$-pregnadiene-3,20-dione
k. 11$\beta$-isobutyroxy-16$\alpha$,17$\alpha$,21-trimethyl-$\Delta^{1,4}$-pregnadiene-3,20-dione
l. 6$\alpha$,16$\alpha$,17$\alpha$,21-tetramethyl-11$\beta$-hydroxy-$\Delta^{1,4}$-pregnadiene-3,20-dione.

| Dose Compound | Edema % change after 4 hrs 10 mg/kg subcut. | 3 mg/kg subcut. | 1 mg local |
|---|---|---|---|
| a | 0 | n.d. | −11 |
| b | −12 | 0 | −41 |
| c | −28 | −18 | −54 |
| d | −39 | −22 | −64 |
| e | −44 | −33 | −93 |
| f | 0 | 0 | −38 |
| g | −13 | 0 | −36 |
| h | 0 | n.d. | −31 |
| i | −18 | −23 | −71 |
| j | 0 | n.d. | −36 |
| k | −11 | 0 | −36 |
| l | −28 | −18 | −54 | n.d. = not determined.

From these data it is clear that the compounds according to the invention exhibit local anti-inflammatory activity and no or low systemic activity.

The invention is further illustrated by the following examples:

EXAMPLE 1

A mixture of 3$\beta$-hydroxy-16$\alpha$,17$\alpha$-dimethyl-$\Delta^{5}$-pregnen-20-one (25 g), dimethylamine hydrochloride (50 g), paraformaldehyde (15 g) and 2N hydrochloric acid (1.5 ml) was refluxed in iso-amyl alcohol (500 ml) for 2 1/4 hours, then further paraformaldehyde (15 g) was added. After a further hour, the cooled solution was shaken with water, and the crystalline solid thus obtained was filtered, washed with water, then with ether and dried, to give 3$\beta$-hydroxy-16$\alpha$,17$\alpha$-dimethyl-21-dimethylaminomethyl-$\Delta^{5}$-pregnen-20-one hydrochloride (8.0 g).

The filtrate was washed to neutrality with brine, back-extracting the washings with iso-amyl alcohol. The organic phase was concentrated to low volume, diluted with ether/methylene chloride and left overnight in the refrigerator. After filtration, the solid was washed with methylene chloride and dried to give a further crop of the amine hydrochloride (1.0 g).

3$\beta$-Hydroxy-16$\alpha$,17$\alpha$-dimethyl-21-dimethylaminomethyl-$\Delta^{5}$-pregnen-20-one hydrochloride (8.9 g) was suspended in 1.0N potassium hydroxide (450 ml) and shaken with ether (900 ml) and methylene chloride (150 ml) for several minutes. The organic layer was then washed neutral with water, dried and evaporated to give the free amine as a crystalline solid. This was dissolved in methylene chloride (90 ml) and ethyl bromide (18 ml). The solution was allowed to stand overnight, then the quaternary bromide (8.9 g) was filtered off and washed with methylene chloride.

The quaternary bromide salt was dissolved in 25% isopropanol in water (1900 ml) and saturated potassium bicarbonate (115 ml) was added. The fine precipitate which formed was extracted into ether (500 ml), and this extract was washed neutral with water, dried and evaporated to give a solid (6.4 g). This was dissolved in isopropanol (320 ml) and hydrogenated over 10% palladium/charcoal (0.7 g) for 30 minutes. The catalyst was removed by filtration and the solution was diluted with water to give a fine solid, which was extracted into methylene chloride (500 ml), dried and evaporated to give a gummy solid (6.0 g). Crystallisation from acetone/hexane gave pure 3β-hydroxy-16α,17α,21-trimethyl-Δ⁵-pregnen-20-one, m.p. 174°–177°C.

The above procedure, when carried out on 3β-hydroxy-16α,17α-dimethyl-Δ⁹⁽¹¹⁾-5α-pregnen-20-one and 3β-hydroxy-16β,17α-dimethyl-Δ⁹⁽¹¹⁾-5α-pregnen-20-one, furnished 3β-hydroxy-16α,17α,21-trimethyl-Δ⁹⁽¹¹⁾-5α-pregnen-20 -one (m.p. 156°–157°C), and 3β-hydroxy-16β,17α,21-trimethyl-Δ⁹⁽¹¹⁾-5α-pregnen-20-one (m.p. 133°–134°C) respectively.

EXAMPLE 2

To a stirred solution of 3β-hydroxy-16α,17α-dimethyl-Δ⁵-pregnen-20-one (1 g) in sodium-dried tetrahydrofuran (25 ml) under nitrogen was added a solution of trityl lithium in sodium-dried tetrahydrofuran until the red colour of trityl lithium just persisted. Methyl iodide (5 ml) was then added rapidly with vigorous stirring. After 30 minutes the solution was evaporated to dryness under vacuum. The residue, which was then a 3-methyl-ether, was dissolved in ether (10 ml), and acetic anhydride (40 ml) and the solution was cooled to 0°C. Boron trifluoride diethyletherate (7 ml) previously cooled to 0°C, was added and the solution left in a refrigerator overnight, then poured on to ice. The gummy product (by now the 3-acetate) was hydrolysed with potassium carbonate in methanol, purified on a silica column, and crystallised from acetone/hexane to give 3β-hydroxy-16α,17α,21-trimethyl-Δ⁵-pregnen-20-one (0.6 g), m.p. 174°–178°C.

EXAMPLE 3

3βHydroxy-16α,17α-dimethyl-Δ⁵-pregnen-20-one 3-benzoate (1 g) was treated with trityl lithium and methyl iodide as described in Example 2. Hydrolysis with potassium hydroxide in methanol gave a mixture of the 3-alcohol and 3-methyl-ether which was converted to the 3-alcohol as in Example 2. Purification and crystallisation gave 3β-hydroxy-16α,17α,21-trimethyl-Δ⁵-pregnen-20-one (0.7 g) identical with that described in Example 1.

EXAMPLE 4

3β-Hydroxy-16α,17α-dimethyl-Δ⁵-pregnen-20-one 3-tetra-hydropyranyl ether (1.45 g) was treated with trityl lithium and methyl iodide as described in Example 2. The crude product was dissolved in 80% acetic acid (25 ml) and warmed for 30 minutes. The solid which formed on addition of water was isolated by filtration, dried, and crystallised to give 3β-hydroxy-16α,17α,21-trimethyl-Δ⁵-pregnen-20-one (0.85 g) identical with that described in Example 1.

The same procedure when carried out on 3β,11α-dihydroxy-16α,17α-dimethyl-Δ⁵-pregnen-20-one bis-tetrahydropyranyl ether resulted in the production of 3β,11α-dihydroxy-16α,17α,21-trimethyl-Δ⁵-pregnen-20-one (amorphous solid).

EXAMPLE 5

A solution of trityl lithium in dry THF was added to a stirred solution of 3β-hydroxy-16α,17α-dimethyl-Δ⁹⁽¹¹⁾-5α-pregnen-20-one 3tetrahydropyranyl ether (7 g) in dry THF (125 g) under nitrogen at 0°C until a slight excess was present. Dry methyl iodide (25 ml) was then added rapidly with vigorous stirring and after 30 minutes the solution was evaporated to dryness under vacuum. The residue was hydrolysed in 80% acetic acid (60 ml) for 30 minutes on a steambath, cooled, and the product precipitated with water and isolated via ether/methylene chloride. The washed and dried extract was evaporated and the crude product was purified on a silica column and crystallised from acetone/hexane to give 3β-hydroxy-16α,17α,21-trimethyl-Δ⁹⁽¹¹⁾-5α-pregnen-20-one (4.2 g) m.p. 156°–157°C.

The above procedure, when carried out on 16α,17α-dimethyl-Δ⁹⁽¹¹⁾-5α-pregnene-3,20-dione 3-dimethylketal; 16α-methyl-Δ⁹⁽¹¹⁾-5α-pregnene-3,20-dione 3-dimethylketal; 16α-methyl-17α-hydroxy-Δ⁹⁽¹¹⁾-5α-pregnene-3,20-dione 3-dimethyl ketal 17-acetate; 16α-methyl-17α-hydroxy-Δ⁹⁽¹¹⁾-5α-pregnane-3,20-dione 3-dimethyl ketal; 16β,17α-dimethyl-Δ⁹⁽¹¹⁾-5α-pregnane-3,20-dione 3-dimethyl ketal; 16α,17α-dimethyl-Δ⁹⁽¹¹⁾-5β-pregnene-3,20-dione 3-dimethylketal; and 6-fluoro-16α,17α-dimethyl-Δ⁵-pregnene-3,20-dione 3-ethyleneketal, furnished 16α,17α,21-trimethyl-Δ⁹⁽¹¹⁾-5α-pregnene-3,20-dione (m.p. 173°–176°C); 16α,21-dimethyl-Δ⁹⁽¹¹⁾-5α-pregnene-3,20-dione (m.p. 157°–159° C); 16α,21-dimethyl-17α-hydroxy-Δ⁹⁽¹¹⁾-5α-pregnene-3,20-dione 17-acetate (m.p. 198°–204° C); 16α,21-dimethyl-17α-hydroxy-Δ⁹⁽¹¹⁾-5α-pregnene-3,20-dione 17-methylether (m.p. 189°–194° C); 16β,17α,21-trimethyl-Δ⁹⁽¹¹⁾-5α-pregnene-3,20-dione (m.p. 170°–172° C); 16α,17α,21-trimethyl-Δ⁹⁽¹¹⁾-5β -pregnene-3,20-dione (m.p. 185°–189° C); and 6α-fluoro-16α,17α,21-trimethyl-Δ⁴-pregnene-3,20-dione (m.p. 193.5°–197.5° C), respectively.

EXAMPLE 6

To a stirred solution of 3β-hydroxy-16α,17α-dimethyl-21-bromo-Δ⁵-pregnen-20-one 3-acetate (10 g) in sodium-dried tetrahydrofuran (250 ml) under nitrogen was added dropwise methyl magnesium chloride (1.0N in tetrahydrofuran, 35 ml). After 5 minutes, dry methyl iodide (50 ml) was added and the solution was heated under reflux overnight. The methyl iodide was removed by evaporating and the cooled residue was poured into ammonium chloride solution. The product, after hydrolysis by potassium hydroxide in methanol, was a mixture of 3β-hydroxy-16α,17α-dimethyl-Δ⁵-pregnen-20-one, 3β-hydroxy-16α,17α,21-trimethyl-Δ⁵-pregnen-20-one, and 3β-hydroxy-16α,17α, 21,21-tetramethyl-Δ⁵-pregnen-20-one. Chromatography on silica gave a mixture of the trimethyl and tetramethyl derivatives which was purified by crystallisation from acetone/hexane to give 3β-hydroxy-16α,17α,21 trimethyl-Δ⁵-pregnen-20-one (2.0 g) (m.p. 174°–177° C) identical with that described in Example 1.

EXAMPLE 7

To stirred liquid ammonia (400 ml) refluxing under a drikold condenser, was added sodium (3.3 g) in small pieces. When the blue colour of the sodium solution had been discharged (this was catalysed by the addition of a ferric salt) 3β-hydroxy-16α,17α-dimethyl-Δ⁵-pregnen-20-one (10 g) dissolved in sodium-dried tetrahydrofuran (200 ml) was added dropwise. After stirring for 1.75 hours, dry methyl iodide (50 ml) diluted with tetrahydrofuran (200 ml) was added dropwise. The solution was then stirred overnight, allowing the ammonia to evaporate. The residue was treated with a solution of ammonium chloride (6.0 g) in water (200 ml) and the mixture was extracted with ether (500 ml).

The aqueous layer was again extracted with ether (2 × 250 ml), and the combined ethereal extracts were washed with dilute hydrochloric acid, sodium thiosulphate solution, and water to neutrality, dried and evaporated. The residue was treated with boron trifluoride/acetic anhydride, then hydrolysed to the 3-alcohol as described in Example 2. The product was a mixture of starting material, 3β-hydroxy-16α,17α,21-trimethyl-$\Delta^5$-pregnen-20-one, and a small amount of 3β-hydroxy-16α,17α,21,21-tetramethyl-$\Delta^5$-pregnen-20-one, from which 3β-hydroxy-16α,17α,21-trimethyl-$\Delta^5$-pregnen-20-one (3.5 g), m.p. 174°–177° C was isolated by the method described in Example 6, and shown to be identical with the sample described in Example 1.

EXAMPLE 8

A solution of 3β,11β-dihydroxy-16α,17α-dimethyl-5α-pregnan-20-one 3-tetrahydropyranyl ether 11-acetate (2 g) in dry tetrahydrofuran (20 ml) was added to a stirred solution of lithium di-isopropylamide (1.1 mole equivalents) in tetrahydrofuran (20 ml) under nitrogen at −25° C. After 30 minutes, the solution was allowed to warm to −5° C, methyl iodide (10 ml) was added and the reaction allowed to warm to room temperature, after which it was evaporated to dryness under reduced pressure. The residue was dissolved in 80% acetic acid and allowed to stand overnight. Addition of water gave a crystalline solid which was filtered, washed with water, dried and crystallised to give b 3β,11β-dihydroxy16α,17α,21-trimethyl-5α-pregnan-20-one 11-acetate (m.p. 178°–181° C).

Repeat of the above procedure on 11β-hydroxy-16α,17α-dimethyl-5α-pregnan-3,20-dione 3-dimethylketal 11-acetate gave 11β-hydroxy-16α,17α,21-trimethyl-5α-pregnane-3,20dione 11-acetate (m.p. 158°–163° C).

EXAMPLE 9

A solution of 3α,11β-dihydroxy-16α,17α-dimethyl-5β-pregnan-20-one 3-tetrahydropyranyl ether 11-acetate (2 g) in dry tetrahydrofuran (20 ml) was added to a stirred solution of lithium di-isopropylamide (2.2 mole equivalents) in tetrahydrofuran under nitrogen at −25° C. The temperature was allowed to rise to −5° C and methyl iodide (10 ml) was added. The product was hydrolysed and worked up as described in Example 8 and isolated via methylene chloride to give a non-crystalline mixture of 3α,11β-dihydroxy 16α,17α,21-trimethyl-5β-pregnan-20-one 11-propionate and 3α,11β-dihydroxy-16α,17α,21-trimethyl-5β-pregnan-20-one 11-isobutyrate (5:1).

The same procedure when carried out on 11β-hydroxy-16α,17α-dimethyl-5β-pregnane-3,20-dione 3-dimethylketal 11-acetate gave a non-crystalline mixture of 11β-hydroxy16α,17α,21-trimethyl-5β-pregnane-3,20-dione 11-propionate and 11β-hydroxy-16α,17α,21-trimethyl-5β-pregnane-3,20-dione 11-isobutyrate.

EXAMPLE 10

A solution of 3β-hydroxy-16α,17α,21-trimethyl-$\Delta^{9(11)}$-5α-pregnen-20-one (5.2 g) in acetone (50 ml) was treated with 8N chromic acid solution (7 ml) over ten minutes with external cooling. Excess reagent was destroyed with isopropanol and the mixture was filtered, washed and dried to give 16α,17α,21-trimethyl-$\Delta^{9(11)}$-5α-pregnene-3,20-dione (4.9 g), m.p. 173°–176° C.

The above procedure, when carried out on 3β-hydroxy-16β,17α,21-trimethyl-$\Delta^{9(11)}$-pregnen-20-one; and 3β,11β-dihydroxy-16α,17α,21-trimethyl-5α-pregnan-20-one 11-acetate; gave 16β,17α,21-trimethyl-$\Delta^{9(11)}$-5α-pregnene-3,20-dione (m.p. 170°–171.5° C); and 11β-hydroxy-16α,17α,21-trimethyl-5α-pregnane-3,20 11-acetate (m.p. 158°–163° C0 respectively.

EXAMPLE 11

A solution of 16α,17α-dimethyl-$\Delta^{9(11)}$-5α-pregnene-3,20-dione 3-dimethylketal (2 g) in sodium-dried tetrahydrofuran (50 ml) was slowly added to a stirred solution of lithium di-isopropylamide (1.5 mole equivalents; prepared from 1.23 ml di-isopropylamine) in tetrahydrofuran (8 ml) under nitrogen at 0° C. The solution was stirred for 30 minutes, allowing it to warm to room temperature, then was again cooled to 0° C, and methyl iodide (10 ml) was added rapidly with vigorous stirring. The cooling bath was again removed and after stirring for 30 minutes the solution was concentrated under vacuum to remove methyl iodide. 80% Acetic acid (25 ml) was added, and the solution was allowed to stand overnight. The product was precipitated as a crystalline solid by the slow addition of water. It was filtered, washed with water and dried to give 16α,17α,21-trimethyl-$\Delta^{9(11)}$-5α-pregnene-3,20-dione (1.8 g), m.p. 173°–176° C.

EXAMPLE 12

A solution of 16α,17α-dimethyl-$\Delta^{9(11)}$-5α-pregnene-3,20-dione 3-dimethylketal (1 g) in sodium-dried tetrahydrofuran (25 ml) was slowly added to a stirred solution of lithium diethylamide (1.5 mole equivalents; prepared from 0.45 ml diethylamine) in tetrahydrofuran (4 ml) under nitrogen at 0° C. Dry methyl iodide (5 ml) was subsequently added and the reaction was carried out and worked up exactly as described in Example 11 to give 16α,17α,21-trimethyl-$\Delta^{9(11)}$-5α-pregnene-3,20-dione (0.9 g), identical with that prepared in Example 11.

EXAMPLE 13

A solution of 3β-hydroxy-16α,17α,21-trimethyl-$\Delta^5$-pregnen-20-one (10 g) in dry toluene (100 ml) and cyclohexanone (50 ml) was treated with a solution of aluminium isopropoxide (5 g) in toluene (50 ml). The mixture was heated under reflux for 45 min. then cooled and treated with a solution of Rochelle salt (20 g) in water (50 ml). The mixture was steam-distilled until the distillate was clear and the product was filtered, dried, and purified on alumina to give 16α,17α,21-trimethyl-$\Delta^4$-pregnene-3,20-dione (7,72 g; m.p. 165°–170° C).

EXAMPLE 14 a. 16α,17α-Dimethyl-$\Delta^4$-pregnene-3,20-dione (5 g) was suspended in dry dioxan (50 ml) and ethyl orthoformate (5 ml) and p-toluenesulphonic acid (250 mg) added. The mixture was stirred at room temperature for 2.5 hours and a further portion of ethyl orthoformate (5 ml) added. After another hour the reaction was worked up by addition of pyridine (2 ml) followed by 5% potassium carbonate solution (10 ml) then water. The yellow crystalline solid was filtered, washed, dried, and purified on a column of alumina to give 3-ethoxy-16α,17α-dimethyl-$\Delta^{3,5}$-pregnadien-20-one (4.13 g).

b. A solution of 3-ethoxy-16α,17α-dimethyl-$\Delta^{3,5}$-pregnadien-20-one (1 g) in dry tetrahydrofuran (25 ml) was added to a stirred solution of lithium di-isopropylamide (1.5 mole equivalents) in dry tetrahydrofuran (10 ml) at 0°C under nitrogen, and the mixture allowed to come to room temperature. Methyl iodide (5 ml) was then added and the reaction stirred for a further 30 minutes. Excess methyl iodide was evaporated under reduced pressure and the residue poured into sodium sulphite solution. The product was filtered, washed, and dissolved in aqueous acetic acid and heated for 30 minutes on a steam bath. The solid which formed on dilution with water was filtered, washed, dried and purified on silica to give 16α,17α,21trimethyl-$\Delta^4$-pregnene-3,20-dione (m.p. 166°–170°C).

EXAMPLE 15

A solution of 16α,17α-dimethyl-$\Delta^{1,4}$-pregnadiene-3,20-dione (1.0 g) in dry tetrahydrofuran (20 ml) was added to a stirred solution of lithium di-isopropylamide (2.5 mole equivalents) in tetrahydrofuran (20 ml) at 0°C under nitrogen. The solution was allowed to come to room temperature over 30 minutes and then methyl iodide (10 ml) was added. After a further 30 minutes the reaction mixture was diluted with water, the product filtered, washed, dried and purified on an alumina column to give 16α,17α,21-trimethyl-$\Delta^{1,4}$-pregnadiene-3,20-dione (m.p. 164°–165°C).

EXAMPLE 16

To a stirred solution of 16α,17α,21-trimethyl-$\Delta^{9(11)}$-5β-pregnene-3,20-dione (30 g) in chloroform (300 ml) and acetic acid (15 ml) at 0°C was added a solution of hydrogen bromide in acetic acid (6 ml). Bromine (9.3 ml) as a 10% solution in chloroform, was added dropwise followed by 10% sodium acetate solution until the reaction solution was no longer acid to Congo Red.

The organic layer was diluted with methylene chloride, washed with sodium carbonate solution, then with water to neutrality, dried and evaporated to give 2β,4β-dibromo-16α,17α,21-trimethyl-$\Delta^{9(11)}$-5β-pregnene-3,20-dione (45 g). This total product was added to a stirred suspension of calcium carbonate (45 g) and lithium bromide (22.5 g) in dimethylacetamide (900 ml) under nitrogen, boiled for 10 minutes, cooled and poured into stirred water (5000 ml) and acetic acid (90 ml). The product was filtered, washed with water, dissolved in benzene and dried over sodium sulphate, and the dried solution run through an alumina column. The column was washed with ether, and the combined eluates were evaporated to dryness. The residue was purified on a silica column and crystallised from methylene chloride/methanol to give 16α,17α,21-trimethyl-$\Delta^{1,4,9(11)}$-pregnatriene-3,20-dione (9 g), m.p. 170°–175°C.

EXAMPLE 17

16α,17α,21-Trimethyl-$\Delta^{9(11)}$-5α-pregnene-3,20-dione (5.2 g) in toluene (70 ml) was heated under reflux for 18 hours with dichlorodicyanobenzoquinone (7.6 g). The cooled reaction mixture was filtered and the filtrate was washed with water, and potassium carbonate solution, dried over sodium sulphate, and passed through a short column of alumina. The eluate and washings were evaporated to dryness and the residue was dissolved in ethanol (30 ml) containing 10% acetic acid. This solution was refluxed for two hours with Girard's Reagent P (1 g), then poured into dilute sodium hydroxide solution, and extracted into methylene chloride. The extract was washed with water, dried over sodium sulphate, evaporated to dryness, and the residue crystallised from acetone/ether to give 16α,17α,21-tri-methyl-$\Delta^{1,4,9(11)}$-pregnatriene-3,20-dione (2 g), m.p. 170°–175°C.

The above procedure, when carried out on 16α,17α,21-trimethyl-$\Delta^{9(11)}$-5β-pregnene-3,20-dione; 16α,21-dimethyl-$\Delta^{9(11)}$-5α-pregnene-3,20-dione; 16β,17α,21-trimethyl-$\Delta^{9(11)}$-5α-pregnene-3,20-dione; 11β-hydroxy-16α,17α,21-trimethyl-5α-pregnane-3,20-dione 11-acetate and 16α,17α-dimethyl-21-ethyl-$\Delta^{9(11)}$-5α-pregnene-3,20-dione furnished 16α,17α,21-trimethyl-$\Delta^{1,4,9(11)}$-pregnatriene-3,20-dione (m.p. 170°–175°C); 16α, 21-dimethyl-$\Delta^{1,4,9(11)}$-pregnatriene-3,20-dione (m.p. 142°–146°C); 16β,17α,21-trimethyl-$\Delta^{1,4,9(11)}$-pregnatriene-3,20-dione (m.p. 205°–207°C); 11β-hydroxy-16α,17α,21-trimethyl-$\Delta^{1,4}$-pregnadiene-3,20-dione 11-acetate (m.p. 203°–205°C); and 16α,17α-dimethyl-21-ethyl-$\Delta^{1,4,9(11)}$-pregnatriene-3,20-dione (m.p. 129°–132°C) respectively.

EXAMPLE 18

The mixture of 11β-hydroxy-16α,17α,21-trimethyl-5β-pregnane-3,20-dione 11-propionate and 11β-hydroxy-16α,17α,21-trimethyl-5β-pregnane-3,20-dione 11-isobutyrate (1.9 g) (prepared as described in example 9) was dehydrogenated exactly as described in example 17. The crude product was purified by chromatography on silica to give 11β-hydroxy-16α,17α,21-trimethyl-$\Delta^{1,4}$-pregnadiene-3,20-dione 11-propionate (m.p. 152–154°C) and 11β-hydroxy-16α,17α,21-trimethyl-$\Delta^{1,4}$-pregnadiene-3,20-dione 11-isobutyrate (m.p. 189°–197°C).

EXAMPLE 19 a. A solution of 16α,17α,21-trimethyl-$\Delta^{1,4,9(11)}$-pregnatriene-3,20-dione (2 g) in DMF (24 ml) containing perchloric acid (0.4 ml) was stirred at room temperature for two hours with N-bromosuccinimide (1.55 g) in the absence of light. Excess reagent was destroyed with sodium bisulphite solution, and the reaction mixture was poured into water. The product was filtered and dried to give 9α-bromo-11β-hydroxy-16α,17α,21-trimethyl-$\Delta^{1,4}$-pregnadiene formate (2.6 g).

The bromo-formate (2.6 g) was suspended in methanol (30 ml) and stirred under nitrogen with a solution of sodium methoxide in methanol (6 ml; 1.1N) for half an hour. The solution was neutralised with acetic acid and diluted with water. The gummy product was extracted into ether, washed neutral, dried and purified on a short column of alumina, and finally crystallised from ether to give 9β, 11β-epoxy-16α,17α,21-trimethyl-$\Delta^{1,4}$-pregnadiene-3,20-dione (1.5 g), m.p. 125°–131°C.

Repeat of the above procedure on 6α,16α,17α,21-tetramethyl-$\Delta^{1,4,9(11)}$-pregnatriene-3,20-dione; 6α-fluoro-16α,17α,21-trimethyl-$\Delta^{1,4,9(11)}$-pregnatriene-3,20-dione; 16α,17α,21-trimethyl-$\Delta^{4,9(11)}$-pregnadiene-3,20-dione; 16α,21-di-methyl-$\Delta^{1,4,9(11)}$-pregnatriene-3,20-dione; 16β,17α,21-trimethyl-$\Delta^{1,4,9(11)}$-pregnatriene-3,20-dione; and 16α,17α-dimethyl-21-ethyl-$\Delta^{1,4,9(11)}$-pregnatriene-3,20-dione furnished 6α,16α,17α,21-tetramethyl-9β,11β-epoxy-$\Delta^{1,4}$-pregnadiene-3,20-dione; 6α-fluoro-9β,11β-epoxy-16α,17α,21-trimethyl-$\Delta^{1,4}$-pregnadiene-3,20-dione (m.p. 180°–182°

C); 9β,11β-epoxy-16α,17α,21-trimethyl-$\Delta^4$-pregnene-3,20-dione; 9β,11β-epoxy-16α,21-dimethyl-$\Delta^{1,4}$-pregnadiene-3,20-dione (m.p. 153°–158° C); 9β,11β-epoxy-16β,17α,21-trimethyl-$\Delta^{1,4}$-pregnadiene-3,20-dione (m.p. 138°–140°C); and 9β,11β-epoxy-16α,17α-dimethyl-21-ethyl-$\Delta^{1,4}$-pregnadiene-3,20-dione (non-crystallline), respectively.

b. Gaseous hydrogen fluoride was passed into a mixture of ethanol-free dry chloroform (2 ml) and tetrahydrofuran (5 ml) at —40° C until 3 g had been adsorbed. 9β,11β-Epoxy16α,17α,21-trimethyl-$\Delta^{1,4}$-pregnadiene-3,20-dione (1.2 g) in dry chloroform (6 ml) was added to a solution of hydrogen fluoride (3 g) in chloroform (2 ml) and tetrahydrofuran (5 ml) at —40° C and washed in with more chloroform (7 ml). The reaction mixture was left in an ice-bath for four hours, and then poured carefully into ice-water containing potassium carbonate (20 g). The solvent was evaporated and the resulting solid was filtered, washed and dried. The crude product was purified on a silica column and crystallised from acetone/ether to give 9α-fluoro-11β-hydroxy-16α,17α,21-trimethyl-$\Delta^{1,4}$-pregnadiene-3,20-dione (660 mg), m.p. 226°–241° C. The same procedure, when carried out on 6α,16α,17α,21-tetramethyl-9β,11β-epxoy-$\Delta^{1,4}$-pregnadiene-3,20-dione; 6α-fluoro-9β,11β-epoxy-16α,17α,21-trimethyl-$\Delta^{1,4}$-pregnadiene-3,20-dione; 9β,11β-epoxy-16α,17α,21-trimethyl-$\Delta^4$-pregnene-3,20-dione; 9β,11β-epoxy-16α,21-dimethyl-$\Delta^{1,4}$-pregnadiene-3,20-dione; 9β,11β-epoxy-16β,17α,21-trimethyl-$\Delta^{1,4}$-pregnadiene-3,20-dione; and 9β,11β-epoxy-16α,17α-dimethyl-21-ethyl-$\Delta^{1,4}$-pregnadiene-3,20-dione gave 6α,16α,17α,21-tetramethyl-9α-fluoro-11β-hydroxy-$\Delta^{1,4}$-pregnadiene-3,20-dione; 6α,9α-difluoro-11β-hydroxy-16α,17α,21-trimethyl-$\Delta^{1,4}$-pregnadiene-3,20-dione (m.p. 252°–265° C); 9α-fluoro-11β-hydroxy-16α,17α,21-trimethyl-$\Delta^4$-pregnene-3,20-dione (m.p. 215–219° C); 9α-fluoro-11β-hydroxy-16α,21-dimethyl-$\Delta^{1,4}$-pregnadiene-3,20-dione (m.p. 247–248° C); 9α-fluoro-11β-hydroxy-16β,17α,21-trimethyl-$\Delta^{1,4}$-pregnadiene-3,20-dione (m.p. 200–201° C); and 9α-fluoro-11β-hydroxy-16α,17α-dimethyl-21-ethyl-$\Delta^{1,4}$-pregnadiene-3,20-dione (m.p. 212°–221° C), respectively.

EXAMPLE 20

16α,17α,21-Trimethyl-$\Delta^{1,4,9(11)}$-pregnatriene-3,20-dione (500 mg) were dissolved in 10% aqueous dioxan (20 mls) cooled to 10° C and 72% perchloric acid (0.1 ml) was added followed by N-chloro-succinimide (0.3 g) and the reaction stirred overnight. The product was watered out, filtered, dried and recrystallised from methylene chloride to give 9α-chloro-11β-hydroxy-16α,17α,21-trimethyl-$\Delta^{1,4}$-pregnadiene-3,20-dione (350 mg), m.p. 257°–259° C.

EXAMPLE 21

To a stirred solution of 9α-fluoro-11β-hydroxy-16α,17α, 21-trimethyl-$\Delta^{1,4}$-pregnadiene-3,20-dione (500 mg) in acetone (30 ml) at room temperature was slowly added 7.9N Jones' chromic unit reagent (1 ml). After 10 minutes, isopropanol was added to destroy excess reagent, and the product was precipitated by the slow addition of water, filtered and dried. A solution of the solid in methylenen chloride was run through a short column of alumina, evaporated to dryness and the residue crystallised from acetone/hexane to give 9α-fluoro-16α,17α,21-trimethyl-$\Delta^{1,4}$-pregnadiene-3,11,20-trione (440 mg). m.p. 190°–215° C.

When the same process was carried out on 9α-chloro-11β-hydroxy-16α,17α,21-trimethyl-$\Delta^{1,4}$-pregnadiene-3,20-dione; 11β-hydroxy-16α,17α,21-trimethyl-$\Delta^{1,4}$-pregnadiene-3,20-dione; 9α-fluoro-11β-hydroxy-16β,17α,21-trimethyl-$\Delta^{1,4}$-pregnadiene-3,20-dione; 11β-hydroxy-16β,17α,21-trimethyl-$\Delta^{1,4}$-pregnadiene-3,20-dione; and 6α-fluoro-11α-hydroxy-16α,17α,21-trimethyl-$\Delta^{1,4}$-pregnadiene-3,20-dione; the products were 9α-chloro-16α,17α,21-trimethyl-$\Delta^{1,4}$-pregnadiene-3,11,20-trione (m.p. 242°–245° C); 16α,17α,21-trimethyl-$\Delta^{1,4}$-pregnadiene3,11,20-trione (m.p. 247–249° C); 9α-fluoro-16β,17α,21-trimethyl-$\Delta^{1,4}$-pregnadiene-3,11,20-trione (m.p. 154–155° C); 16β,17α,21-trimethyl-$\Delta^{1,4}$-pregnadiene-3,11,20-trione (m.p. 181–182° C); and 6α-fluoro-16α,17α,21-trimethyl-$\Delta^{1,4}$-pregnadiene-3,11,20-trione (m.p. 218°–228° C), respectively.

EXAMPLE 22

A stirred solution of 11β-hydroxy-16α,17α,21-trimethyl$\Delta^{1,4}$-pregnadiene-3,20-dione 11-acetate (22 g) in methanol (460 ml) was hydrolysed by addition of potassium hydroxide solution at room temperature. Excess alkali was neutralised with acetic acid and the product was precipitated with water, filtered, washed, dried, purified on a silica column, and crystallised from methylene chloride/methanol to give 11β-hydroxy-16α,17α,21-trimethyl-$\Delta^{1,4}$-pregnadiene-3,20-dione (m.p. 230°–273°C).

The above procedure, carried out on a mixture of 11β-hydroxy-16α,17α,21-trimethyl-$\Delta^{1,4}$-pregnadiene-3,20-dione 11-propionate and 11-isobutyrate; and on 11β-hydroxy-16α, 17α,21-trimethyl-$\Delta^{1,4,6}$-pregnatriene-3,20-dione 11-ropionate, gave 11β-hydroxy-16α,17α,21-trimethyl-$\Delta^{1,4}$-pregnadiene-3,20-dione (m.p. 230°–273° C) and 11β-hydroxy-16α,17α,21-trimethyl$\Delta^{1,4,6}$-pregnatriene-3,20-dione (m.p. 226°–233° C), respectively.

EXAMPLE 23

A solution of 16α,17α,21-trimethyl-$\Delta^{1,4,9(11)}$-pregnatriene-3,20-dione (2.5 g) in tetrahydrofuran (50 ml) containing perchloric acid was stirred for 1 hour at room temperature with N-bromosuccinimide (1.32 g). Excess reagent was destroyed with sodium bisulphite solution and the reaction mixture poured into water. The product was filtered and dried to give 9α-bromo-11β-hydroxy-16α,17α,21-trimethyl-$\Delta^{1,4}$-pregnadiene-3,20-dione (3.15 g).

The bromohydrin (3.15 g) in dimethylsulphoxide (80 ml) was added to a stirred solution of n-butane thiol (4.7 ml) and chromous acetate (9.5 g) in dimethylsulphoxide (42 ml), left overnight at room temperature and then poured into sodium chloride solution. The product was filtered, dried, and recrystallised from methylene chloride/methanol to give 11β-hydroxy-16α,17α,21-trimethyl-$\Delta^{1,4}$-pregnadiene-3,20-dione (m.p. 230°–269° C).

The same process carried out on 6α,16α,17α,21-tetra-methyl-$\Delta^{1,4,9(11)}$-pregnatriene-3,20-dione; 16β,17α,21-tri-methyl-$\Delta^{1,4,9(11)}$-pregnatriene-3,20-dione; 16α,21-dimethyl-$\Delta^{1,4,9(11)}$-pregnatriene-3,20-dione; and 16α,17α-dimethyl-21-ethyl-$\Delta^{1,4,9(11)}$-pregnatriene-3,20-dione gave 6α,16α,17α,21-tetramethyl-11β-hydroxy-$\Delta^{1,4}$-pregnadiene-3,20-dione; 11β-hydroxy-16β,17α,21-trimethyl-$\Delta^{1,4}$-pregnadiene-3,20-dione (m.p. 232°–240° C); 11β-hydroxy-16α,21-dimethyl-$\Delta^{1,4}$-pregnadiene-3,20-dione (m.p. 201–204°

C); and 11β-hydroxy-16α,17α-dimethyl-21-ethyl-Δ$^{1,4}$-pregnadiene-3,20-dione (m.p. 221°–227° C), respectively.

EXAMPLE 24

A solution of 11β-hydroxy-16α,17α,21-trimethyl-5α-pregnane-3,20-dione 11-acetate (10 g) in acetic acid (100 ml) was treated with a 10% solution of bromine in acetic acid (2.73 ml). When reaction was complete, sodium acetate solution was added and the resulting solid filtered, washed and dried to give the crude product (12 g).

The crude mono-brominated product was added to a hot stirred mixture of dimethylformamide (100 ml) lithium bromide (2.5 g) and calcium carbonate (5 g) under nitrogen. After 10 minutes the reaction mixture was cooled, poured into aqueous acetic acid and the product filtered, washed and dried.

The crude product (9.2 g) was heated under reflux for 8 hrs. with methanolic potassium hydroxide, cooled, neutralised with acetic acid, and poured into water. The product was filtered, washed with water, dried and purified by chromatography on silica gel to give 11β-hydroxy-16α,17α, 21-trimethyl-Δ$^4$-pregnene-3,20-dione (m.p. 200°–202° C) and 11β-hydroxy-16α,17α,21-trimethyl-Δ$^1$-5α-pregnene-3,20-dione (m.p. 235°–243° C).

The above procedure carried out on 11β-hydroxy-16α,17α, 21-trimethyl-5β-pregnane-3,20-dione 11-propionate gave a mixture of 11β-hydroxy-16α,17α,21-trimethyl-Δ$^4$-pregnene-3,20-dione (m.p. 200–202° C) and 11β-hydroxy-16α,17α,21-trimethyl-Δ$^1$-5β-pregnene-3,20-dione (m.p. 252°–265° C).

EXAMPLE 25

11β-Hydroxy-16α,17α,21-trimethyl-Δ$^4$-pregnene-3,20-dione 11-propionate (3 q) and dichlorodicyanoquinone (1.94 g) were dissolved in dioxan (50 ml). Hydrogen chloride gas was passed into the solution until a precipitate started to form and the reaction mixture was allowed to stand for a further 20 minutes. The solid was removed by filtration and the filtrate was poured into aqueous sodium carbonate solution. The product was isolated via ether and purified by chromatography on silica gel to give 11β-hydroxy-16α, 17α,21-trimethyl-Δ$^{4,6}$-pregnadiene-3,20-dione 11-propionate (2 g) as an amorphous solid.

The same procedure when carried out on 9α-fluoro-11β-hydroxy-16α,17α,21-trimethyl-Δ$^4$-pregnene-3,20-dione and 9α-fluoro-11β-hydroxy-16α,17α,21-trimethyl-Δ$^{1,4}$-pregnadiene-3,20-dione gave 9α-fluoro-11β-hydroxy-16α,17α,21-trimethyl-Δ$^{4,6}$-pregnadiene-3,20-dione (m.p. 275–283°C) and 9α-fluoro-11β-hydroxy-16α,17α,21-trimethyl-Δ$^{1,4,6}$-pregnatriene-3,20-dione (m.p. 207°–230°C), respectively.

EXAMPLE 26

A solution of 11β-hydroxy-16α,17α,21-trimethyl-Δ$^{4,6}$-pregnadiene-3,20-dione 11-propionate (1.8 g) in dioxan (40 ml) containing dichlorodicyanoquinone (1.3 g) was refluxed overnight. The cooled reaction mixture was worked up as described in Example 17 to give 11β-hydroxy-16α,17α,21-trimethyl-Δ$^{1,4,6}$-pregnatriene-3,20-dione 11-propionate (m.p. 180°–189°C).

EXAMPLE 27 a. A solution of crude 3β,11α-dihydroxy-16α,17α,21-trimethyl-Δ$^5$-pregnen-20-one (22 g) from Example 4 in chloroform (220 ml) was stirred with peracetic acid (22 ml) and sodium acetate (2.2 g) for one hour, after which excess peracid was destroyed by careful addition of sodium sulphite solution. The organic phase was washed neutral, dried over sodium sulphate, and evaporated to dryness. The gummy residue was acetylated and purified first by chromatography on silica and then by crystallisation from methanol to give 3β,11α-dihydroxy-5α,6α-epoxy-16α,17α,21-trimethyl-5α-pregnan-20-one diacetate (10.5 g), m.p. 179°–183°C.

b. 3β,11α-Dihydroxy-5α,6α-epoxy-16α,17α,21-trimethyl-5α-pregnan-20-one diacetate (5 g) was dissolved in diglyme (50 ml) and treated with boron trifluoride etherate (5 ml) and a solution of hydrogen fluoride in diglyme (4 ml of 9N). After five minutes the reaction mixture was poured into water (500 ml) containing sodium acetate (5 g). The product was filtered and dried to give 3β,5α,11α-trihydroxy-6β-fluoro-16α,17α,21-trimethyl-5αpregnan-20-one 3,11-diacetate (5.2 g) as an amorphous solid which could not be crystallised.

c. 3β,5α,11α-Trihydroxy-6β-fluoro-16α,17α,21-trimethyl-5α-pregnan-20-one 3,11-diacetate (5.2 g) was dissolved in methanol (50 ml) and 70% perchloric acid (5 ml). After 3 hours, the reaction mixture was buffered with sodium acetate, concentrated and poured into water (250 ml). The product was extracted into ether, washed neutral, dried and evaporated to dryness. The crude product was purified by chromatography on a silica column to give 3β,5α,11α-trihydroxy-6β-fluoro-16α,17α,21-trimethyl-5α-pregnan-20-one 11-acetate (4 g) as a clear gum which could not be crystallised.

d. A solution of 3β,5α,11α-trihydroxy-6β-fluoro-16α,17α,21-trimethyl-5α-pregnan-20-one 11-acetate in acetone (20 ml) was treated with 8N chromic acid solution (3 ml) dropwise with stirring and external cooling. When the oxidation was complete, methanol was added to decompose excess reagent and the reaction mixture was diluted with water (200 ml) to give a gummy product which was extracted into methylene chloride/ether. The washed and dried extract was evaporated to dryness to give 5α,11α-dihydroxy-6β-fluoro-16α,17α,21-trimethyl-5α-pregnane-3,20-dione 11-acetate (3.8 g) as an intractable gum.

e. 5α,11α-Dihydroxy-6β-fluoro-16α,17α,21-trimethyl-5α-pregnan-20-one 11-acetate (3.8 g) was dissolved in acetic acid (20 ml), and hydrogen chloride gas was passed into the solution for ten minutes. After standing at room temperature for fifteen hours, the solution was poured into water (250 ml) and the product was extracted into methylene chloride/ether. The extract was washed neutral, dried and evaporated to dryness. The crude product was purified on a short column of alumina and crystallised from acetone/ether to give 6α-fluoro-11α-hydroxy-16α,17α,21-trimethyl-Δ$^4$-pregnene-3,20-dione acetate (2.8 g), m.p. 174°–178°C.

EXAMPLE 28

6α-Fluoro-11α-hydroxy-16α,17α,21-trimethyl-Δ$^4$-pregnene- 3,20-dione acetate (2.7 g) in benzene (30 -pregnene-was heated under reflux for 15 hours with 2,3-dichloro-5,6-dicyano-benzoquinone (1.7 g). The reaction mixture was cooled, filtered, and the filtrate was evaporated to dryness. The crude product was purified on a short column of alumina and crystallised to give 6α-fluoro-11α-hydroxy-16α,17α,21-trimethyl-Δ$^{1,4}$-pregnadiene-3,20-dione acetate (1.75 g), m.p.

136°–144°C.

EXAMPLE 29

6α-Fluoro-11α-hydroxy-16α,17α,21-trimethyl-Δ$^{1,4}$-pregnadiene-3,20-dione acetate (1.6 g) was dissolved in methanol (30 ml) and heated at reflux with potassium carbonate (0.5 g) for one hour. The solution was cooled, acidified, poured into water and the solid filtered, washed and dried to give 6α-fluoro-11α-hydroxy-16α,17α,21-trimethyl-Δ$^{1,4}$-pregnadiene-3,20-dione (1.4 g), m.p. 175°–182°C.

EXAMPLE 30 a. 6α-Fluoro-11α-hydroxy-16α,17α,21-trimethyl-Δ$^{1,4}$-pregnadiene-3,20-dione (1.4 g) was dissolved in pyridine (10 ml), cooled to 0°C and treated with methane sulphonyl chloride (0.8 ml). The reaction was allowed to stand at 0°C for 16 hours. The reaction mixture was poured onto ice and the product was filtered, washed and dried to give 6α-fluoro-11α-hydroxy-16α,17α,21-trimethyl-Δ$^{1,4}$-pregnadiene-3,20-dione 11-mesylate which was not purified further.

b. Crude 6α-fluoro-11α-hydroxy-16α,17α,21-trimethyl-Δ$^{1,4}$-pregnadiene-3,20dione 11-mesylate (1.75 g) was dissolved in dimethylformamide (30 ml) containing anhydrous sodium acetate (1.5 g) and heated at reflux for two hours. The reaction mixture was cooled, poured into water (500 ml), and the crude product was filtered, washed and dissolved in methylene chloride. The solution was dried, evaporated to dryness, and the product was purified on a short column of alumina and crystallised from methanol to give 6α-fluoro-16α,17α,21-trimethyl-Δ$^{1,4,9(11)}$-pregnatriene-3,20-dione (0.82 g), m.p. 192°–202°C.

EXAMPLE 31

3β,11α-Dihydroxy-5α,6α-epoxy-16α,17α,21-trimethyl-5α-pregnan-20-one diacetate (5 g) dissolved in sodium-dried benzene (100 ml) was added over fifteen minutes to a stirred solution of methyl magnesium bromide (made from 2 g of magnesium) in ether (35 ml) under nitrogen. During the addition, the reaction was heated so that the ether slowly distilled and after the addition was complete, further sodium-dried benzene was added and heating continued with distillation until the vapour temperature had reached 80°c. The reaction was then refluxed for six hours.

The cooled mixture was poured into ice water containing 5N sulphuric acid (25 ml) and the organic phase was separated, washed neutral, dried over sodium sulphate, and evaporated to dryness. The residue was reacetylated with pyridine/acetic anhydride in the usual way, and purified on a column of silica to give 3β,5α,11α-trihydroxy-6β,16α,17α,21-tetramethyl-5α-pregnan-20-one, 3,11-diacetate (4.9 g) as an intractable gum.

This product was converted by the same series of reactions as described in Examples 27(c) – 30(b) to give 6α,16α,17α,21-tetramethyl-Δ$^{1,4,9(11)}$-pregnatriene-3,20-dione, m.p. 160°–165°C.

EXAMPLE 32 a. A solution of 3β-hydroxy-16α,17α,21-trimethyl-Δ$^5$-pregnen-20-one (20 g) in chloroform (200 ml) at 0°C was treated with peracetic acid (20 ml) containing sodium acetate (2 g). The stirred solution was allowed to warm up to room temperature and after 1.5 hours the reaction was cooled to 5°C and treated with sodium sulphite solution. The product was extracted with methylene chloride, washed, dried and evaporated to dryness. The gummy residue was acetylated and crystallised from methylene chloride/methanol to give 3β-hydroxy-5α,6α-epoxy-16α,17α,21-trimethyl-5α-pregnan-20-one 3-acetate (m.p. 180°–186°C).

b. 3β-Hydroxy-5α,6α-epoxy-16α,17α,21-trimethyl-5α-pregnen-20-one 3-acetate (15 g) was treated with methyl magnesium bromide exactly as described in Example 31.

The cooled mixture was worked up in the usual way to give 3β,5α-dihydroxy-6β,16α,17α,21-tetramethyl-5α-pregnan-20-one.

The crude 3β,5α-diol (14.5 g) in acetone (450 ml) was oxidised with 8N chromic acid solution by the procedure described in Example 27(d), to give 5α-hydroxy-6β,16α,17α,21-tetramethyl-5α-pregnan-3,20-dione. Crude 5α-hydroxy-6β,16α,17α,21-tetramethyl-5α-pregnan-3,20-dione (13.9 g) was stirred overnight in acetic acid (200 ml) containing hydrogen chloride at room temperature and worked up to give 6α,16α,17α,21-tetra-methyl-Δ$^4$-pregnene-3,20-dione (m.p. 162–166°C).

EXAMPLE 33

A solution of 6α-fluoro-16α,17α,21-trimethyl-Δ$^4$-pregnene-3,20-dione (3.35 g) and 2,3-dichloro-5,6-dicyano-benzoquinone (2.44 g) in benzene (50 ml) was heated under reflux with stirring overnight. The solution was cooled and the hydroquinone was removed by filtration. The filtrate was diluted with benzene, washed with water, potassium bicarbonate solution, then with brine to neutrality, dried, concentrated under vacuum and passed through a column of alumina, washing through with ether. The solvent was evaporated and the residue was crystallised from methylene chloride/methanol to give 6α-fluoro-16α,17α,21-trimethyl-Δ$^{1,4}$-pregnadiene-3,20-dione (2.35 g), m.p. 190°–193°C.

The above procedure, when carried out on a 6α,16α,17α,21-tetramethyl-Δ$^4$-pregnene-3,20-dione gave 6α,16α,17α,21-tetramethyl-Δ$^{1,4}$-pregnadiene-3,20-dione (m.p. 149°–156°C) and when carried out on 16α,17α,21-trimethyl-Δ$^4$-pregnen-3,20-dione gave 16α,17α,21-trimethyl-Δ$^{1,4}$-pregnadiene-3,20-dione.

EXAMPLE 34

A solution of 16α,17α-dimethyl-Δ$^{9(11)}$-5α-pregnene-3,20-dione 3-dimethylketal (2 g) in sodium-dried tetrahydrofuran (50 ml) was slowly added to a stirred solution of lithium diisopropylamide (1.5 mole equivalents; prepared from 1.23 ml di-isopropylamine) in tetrahydrofuran (8 ml) under nitrogen at 0°C. The solution was stirred for 30 minutes, allowing it to warm to room temperature, then was again cooled to 0°C, and ethyl iodide (12 ml) was added rapidly with vigorous stirring. The cooling bath was again removed, and after a further 30 minutes, the solution was evaporated to dryness. The residue was dissolved in 80% acetic acid (25 ml) and after 30 minutes on a steam bath the product was precipitated by the slow addition of water. The product was filtered, washed with water, dried and crystallised from acetone/hexane to give 16α,17α-dimethyl-21-ethyl-Δ$^{9(11)}$-5α-pregnene-3,20-dione (1.8 g), m.p. 150°–160°C.

EXAMPLE 35 a. A suspension of 16α,21-dimethyl-17α-hydroxy-Δ$^{9(11)}$-5α-pregnene-3,20-dione (10 g), obtained by hydrolysis of the corresponding 17-acetate of Example 5, and p-toluene-sulphonic acid (1 g) in propionic anhydride (200 ml) was stirred at room temperature. After 1 day solution was complete and after 6 days the solution was poured into stirred ice-water and a little pyridine was added. The mixture was stirred until hydrolysis of the propionic anhydride was complete, then the solid product was filtered off, washed to neutrality with water and dried. The crude product was dissolved in methylene chloride and the solution was passed through a short alumina column then evaporated to dryness. The residue was crystallised from acetone/ether to give 16α,21-di-methyl-17α-hydroxy-Δ$^{9(11)}$-5α-pregnene-3,20-dione-17α-propionate. In a similar manner 16α,21-dimethyl-17α-hydroxy-Δ$^{9(11)}$-5α-pregnene-3,20-dione was converted to 16α,21-dimethyl-17α-hydroxy-Δ$^{9(11)}$-5α-pregnene-3,20-dione 17α-n-valerate.

b. A solution of crude 16α,21-dimethyl-17α-hydroxy-Δ$^{9(11)}$-5α-pregnene-3,20-dione and dichlorodicyano-benzoquinone (2.4 mole equivalents) in 10/1 toluene/acetic acid was heated to reflux overnight. The reaction mixture was then filtered and the filtrate evaporated to dryness, and purged three times with toluene to remove acetic acid. The residue was dissolved in methylene chloride and the solution passed through a short alumina column and washed through with methylene chloride and ether. The eluant was evaporated to give a solid which was purified by chromatography on silica and crystallisation from methylene chloride/methanol to give 16α,21-dimethyl-17α-hydroxy-Δ$^{1,4,9(11)}$-pregnatriene-3,20-dione. M.p. 201°–220°C.

In a similar way: 16α,21-dimethyl-17α-hydroxy-Δ$^{9(11)}$-5α-pregnene-3,20-dione 17α-propionate and 16α,21-dimethyl-17α-hydroxy-Δ$^{9(11)}$-5α-pregnene-3,20-dione 17α-n-valerate were converted to 16α,21-dimethyl-17α-hydroxy-Δ$^{1,4,9(11)}$-pregnatriene-3,20-dione 17α-propionate and 16α,21-dimethyl-17α-hydroxy-Δ$^{1,4,9(11)}$-pregnatriene-3,20-dione 17α-n-valerate, respectively.

c. To a stirred solution of 16α,21-dimethyl-17α-hydroxy-Δ$^{1,4,9(11)}$-pregnatriene-3,20-dione (2 g) in tetrahydro-furan was slowly added 0.5N perchloric acid (10 ml) followed by N-bromoacetamide (1 g) with the exclusion of light. After 30 minutes sodium sulphite solution was added and the mixture was poured into water. The solid product was filtered and dried to give 9α-bromo-11β,17α-dihydroxy-16α,21-dimethyl-Δ$^{1,4}$-pregnadiene-3,20-dione.

In a similar way: 16α,21-dimethyl-17α-hydroxy-Δ$^{1,4,9(11)}$-pregnatriene-3,20-dione 17α-propionate and 16α,21-dimethyl-17α-hydroxy-Δ$^{1,4,9(11)}$-pregnatriene-3,20-dione 17α-n-valerate were converted to 9α-bromo-11β,17α-dihydroxy-16α,21-dimethyl-Δ$^{1,4}$-pregnadiene-3,20-dione 17α-propionate and 9α-bromo-11β,17α-dihydroxy-16α,21-dimethyl-Δ$^{1,4}$-pregnadiene-3,20-dione 17α-n-valerate, respectively.

d. To a stirred solution of n-butanethiol (3 ml) in dimethyl sulphoxide under oxygen-free nitrogen was added freshly prepared chromous acetate (4 g), followed by a solution of 9α-bromo-11β,17α-dihydroxy-16α,21-dimethyl-Δ$^{1,4}$-pregnadiene-3,20-dione (2 g) in dimethyl sulphoxide. The reaction flask was stoppered and the solution stirred overnight magnetically. The mixture was then poured into saturated sodium chloride solution and extracted into ethyl acetate. The extract was washed with 5% sodium carbonate solution, then to neutrality with water, dried and evaporated. The residue was crystallised from methylene chloride/methanol to give 11β,17α-dihydroxy-16α,21-dimethyl-Δ$^{1,4}$-pregnadiene-3,20-dione. M.p. 215°–235°C.

In a similar manner 9α-bromo-11β,17α-dihydroxy-16α,21-dimethyl-Δ$^{1,4}$-pregnadiene-3,20-dione 17α-propionate and 9α-bromo-11β,17α-di-hydroxy-16α,21-dimethyl-Δ$^{1,4}$-pregnadiene-3,20-dione 17α-n-valerate were converted to 11β,17α-dihydroxy-16α,21-dimethyl-Δ$^{1,4}$-pregnadiene-3,20-dione 17α-propionate (m.p. 212°–220°C); and 11β,17α-dihydroxy-16α,21-dimethyl-Δ$^{1,4}$-pregnadiene-3,20-dione 17α-n-valerate (m.p. 152°–156°C).

EXAMPLE 36 a. To a stirred suspension of 9α-bromo-11β,17α-dihydroxy-16α,21-dimethyl-Δ$^{1,4}$-pregnadiene-3,20-dione in methanol under nitrogen was added a slight excess of 0.5 N sodium methoxide solution. After 1 hour the solution was acidified with acetic acid and poured into water. The solid product was filtered and dried to give 9β,11β-epoxy-16α,21-dimethyl-17α-hydroxy-Δ$^{1,4}$-pregnadiene-3,20-dione.

In a similar manner 9α-bromo-11β,17α-dihydroxy-16α,21-dimethyl-Δ$^{1,4}$-pregnadiene-3,20-dione 17α-propionate and 9α-bromo-18β,17α-dihydroxy-16α,21-dimethyl-Δ$^{1,4}$-pregnadiene-3,20-dione 17α-n-valerate were converted to 9β,11β-epoxy-16α,21-dimethyl-17α-hydroxy-Δ$^{1,4}$-pregnadiene-3,20-dione 17α-propionate and 9β,11β-epoxy-16α,21-dimethyl-17α-hydroxy-Δ$^{1,4}$-pregnadiene-3,20-dione 17α-n-valerate.

b. Hydrogen fluoride gas (5 g) was passed into a cooled mixture of tetrahydrofuran and ethanol-free chloroform, and a solution of 9β,11β-epoxy-16α,21-dimethyl-17α-hydroxy-Δ$^{1,4}$-pregnadiene-3,20-dione (2 g) in chloroform was added. Added being allowed to stand for 4 hours at 0°C the solution was poured into stirred sodium acetate solution and the volatile solvent removed under vacuum. The solid product was filtered, dried and crystallised from methylene chloride/methanol to give 9α-fluoro-11β,17α-dihydroxy-16α,21-dimethyl-Δ$^{1,4}$-pregnadiene-3,20-dione. M.p. 238°–261°C.

In a similar manner 9β,11β-epoxy-16α,21-dimethyl-17α-hydroxy-Δ$^{1,4}$-pregnadiene-3,20-dione 17α-propionate and 9β,11β-epoxy-16α,21-dimethyl-17α-hydroxy-Δ$^{1,4}$-pregnadiene-3,20-dione 17α-n-valerate were converted to 9α-fluoro-11β,17α-dihydroxy-16α,21-dimethyl-Δ$^{1,4}$-pregnadiene-3,20-dione 17α-propionate (m.p. 237°–251°C) and 9α-fluoro-11β,17α-dihydroxy-16α,21-dimethyl-Δ$^{1,4}$-pregnadiene-3,20-dione 17α-n-valerate.

EXAMPLE 37

A solution of 9α-fluoro-11β,17α-dihydroxy-16α,21-dimethyl-Δ$^{1,4}$-pregnadiene-3,20-dione in acetone was treated with excess 6.24N Jones Reagent (chromic acid in sulphuric acid). After a few minutes isopropanol was added to consume excess Reagent and the reaction mixture was poured into water. The volatile solvent was removed under vacuum, and the solid product was filtered, dried and crystallised from acetone/hexane to give 9α-fluoro-16α,21-dimethyl-17α-hydroxy-Δ$^{1,4}$-pregnadiene-3,11,20-trione. M.p. 223°–245° C.

What is claimed is:

1. An alkylated 3,20-diketo-Δ$^4$-steroid of the pregnane series having the general formula:

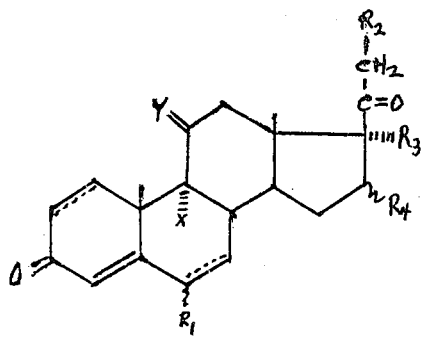

, wherein

X = a member of the group consisting of H, F and Cl;
Y = a member of the group consisting of H(OH), H(OAcyl), the acyl group being derived from a lower alkanoic acid, and 0;
$R_1$ = a member of the group consisting of H, $CH_3$, F, and Cl;
$R_2$ = a member of the group consisting of $CH_3$ and $C_2H_5$;
$R_3$ = a member of the group consisting of H, OAcyl, the acyl group being derived from an organic carboxylic acid having 1-18 carbon atoms, $OCH_3$ and $CH_3$;
$R_4$ = a member of the group consisting of H and alkyl having 1-4 carbon atoms, with the proviso that $R_4$ is alkyl when $R_3$ is other than $CH_3$; and
$C_1$–$C_2$ and $C_6$–$C_7$ are selected from a saturated and an unsaturated bond.

2. A steroid of the formula:

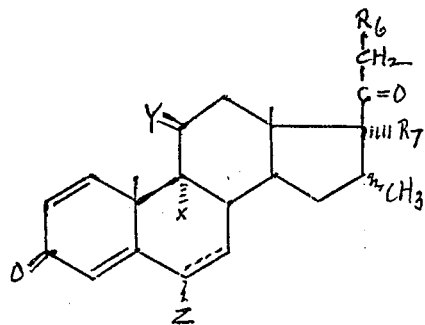

X and Y have the meanings defined in claim 1;
Z = a member of the group consisting of H, $CH_3$, F and Cl;
$R_6$ = a member of the group consisting of $CH_3$ and $C_2H_5$;
$R_7$ = a member of the group consisting of $CH_3$ and OAcyl, the acyl group being derived from an organic carboxylic acid having 1-18 carbon atoms; and
$C_6$–$C_7$ is selected from a saturated and an unsaturated bond.

3. 11β-Hydroxy-16α,17α,21-trimethyl-$\Delta^{1,4}$-pregnadiene-3,20-dione.

4. 9α-Fluoro-11β-hydroxy-16α,17α,21-trimethyl-$\Delta^{1,4}$-pregnadiene-3,20-dione.

5. 11β-Hydroxy-16α,17α,21-trimethyl-$\Delta^{1,4}$-pregnadiene-3,20-dione-11β-isobutyrate.

6. 16β,17α,21-Trimethyl-$\Delta^{1,4}$-pregnadiene-3,11,20-trione.

7. 6α,16α,17α,21-Tetramethyl-$\Delta^4$-pregnene-3,20-dione.

8. 11β-Hydroxy-16α,17α-dimethyl-21-ethyl-$\Delta^{1,4}$-pregnadiene-3,20-dione.

9. 9α-Fluoro-11β-hydroxy-16α,17α,21-trimethyl-$\alpha^{1,4,6}$-pregnatriene-3,20-dione.

10. 11β,17α-Dihydroxy-16α,21-dimethyl-$\Delta^{1,4}$-pregnadiene-3,20-dione 17α-propionate.

11. 9α-Fluoro-11β,17α-dihydroxy-16α,21-dimethyl-$\Delta^{1,4}$-pregnadiene-3,20-dione 17α-n-valerate.

* * * * *

UNITED STATES PATENT OFFICE
CERTIFICATE OF CORRECTION

Patent No. 3,947,478　　　　　　　　　　Dated March 30, 1976

Inventor(s)　Gilbert Frederick Woods et al.

It is certified that error appears in the above-identified patent and that said Letters Patent are hereby corrected as shown below:

Claim 9, line 2, "$\alpha$" should read --$\Delta$--.

Signed and Sealed this eighth Day of June 1976

[SEAL]

Attest:

RUTH C. MASON
*Attesting Officer*

C. MARSHALL DANN
*Commissioner of Patents and Trademarks*